(12) United States Patent
Marziali et al.

(10) Patent No.: US 7,955,865 B2
(45) Date of Patent: Jun. 7, 2011

(54) REAGENT DELIVERY APPARATUS AND METHODS

(75) Inventors: Andrea Marziali, North Vancouver (CA); Diponkar Banerjee, West Vancouver (CA); Jason Donald Thompson, Vancouver (CA); Kurtis Dan Guggenheimer, Abbotsford (CA); Jared Raymond Slobodan, Vancouver (CA); Roy Alexander Belak, Vancouver (CA); David Keddie Brown, Vancouver (CA)

(73) Assignee: The University of British Columbia, Vancouver (CA)

(*) Notice: Subject to any disclaimer, the term of this patent is extended or adjusted under 35 U.S.C. 154(b) by 1188 days.

(21) Appl. No.: 11/570,232

(22) PCT Filed: Jun. 9, 2005

(86) PCT No.: PCT/CA2005/000897
§ 371 (c)(1),
(2), (4) Date: Dec. 7, 2006

(87) PCT Pub. No.: WO2005/121746
PCT Pub. Date: Dec. 22, 2005

(65) Prior Publication Data
US 2008/0047368 A1   Feb. 28, 2008

Related U.S. Application Data

(60) Provisional application No. 60/577,928, filed on Jun. 9, 2004.

(51) Int. Cl.
*B01L 3/02* (2006.01)

(52) U.S. Cl. ........ 436/180; 422/501; 422/509; 422/519; 422/524; 73/864.01; 73/864.22; 73/864.24; 73/864.25

(58) Field of Classification Search .................. 422/100, 422/501, 509, 519, 524; 436/180; 73/864.01–864.25
See application file for complete search history.

(56) References Cited

U.S. PATENT DOCUMENTS

| | | | |
|---|---|---|---|
| 4,661,368 A | 4/1987 | Rohde et al. | |
| 4,737,344 A | 4/1988 | Koizumi et al. | |
| 4,762,578 A | 8/1988 | Burgin, Jr. et al. | |
| 4,794,085 A | 12/1988 | Jessop et al. | |
| 5,143,849 A | 9/1992 | Barry et al. | |
| 2001/0049148 A1* | 12/2001 | Wolk et al. | 436/180 |

OTHER PUBLICATIONS

International Search Report for PCT/CA2005/000897, International Searching Authority, Oct. 6, 2005, pp. 1-5.

* cited by examiner

*Primary Examiner* — Jan M Ludlow
(74) *Attorney, Agent, or Firm* — Oyen Wiggs Green & Mutala LLP

(57) ABSTRACT

Apparatus for dispensing droplets of reagent onto samples includes a probe tip to which droplets of reagent can adhere. The apparatus advances the probe tip toward a sample until a droplet of reagent touches the sample and is pulled off from the probe tip. A sensor detects that the droplet has been pulled off from the probe tip and halts the advance of the probe tip before the probe tip touches the sample. Such apparatus may be used to automatically dispense small volumes of reagent onto fragile samples.

50 Claims, 15 Drawing Sheets

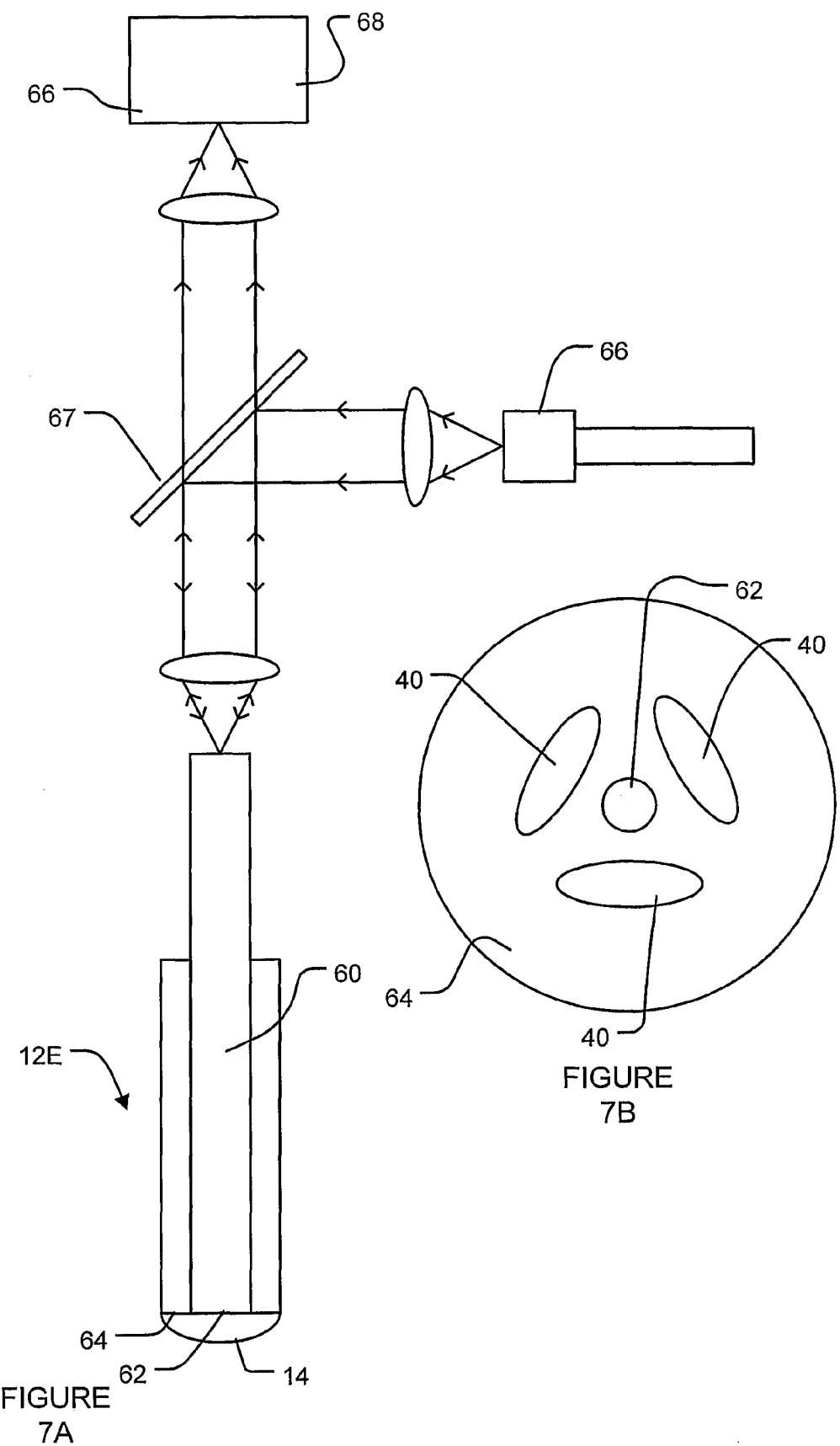

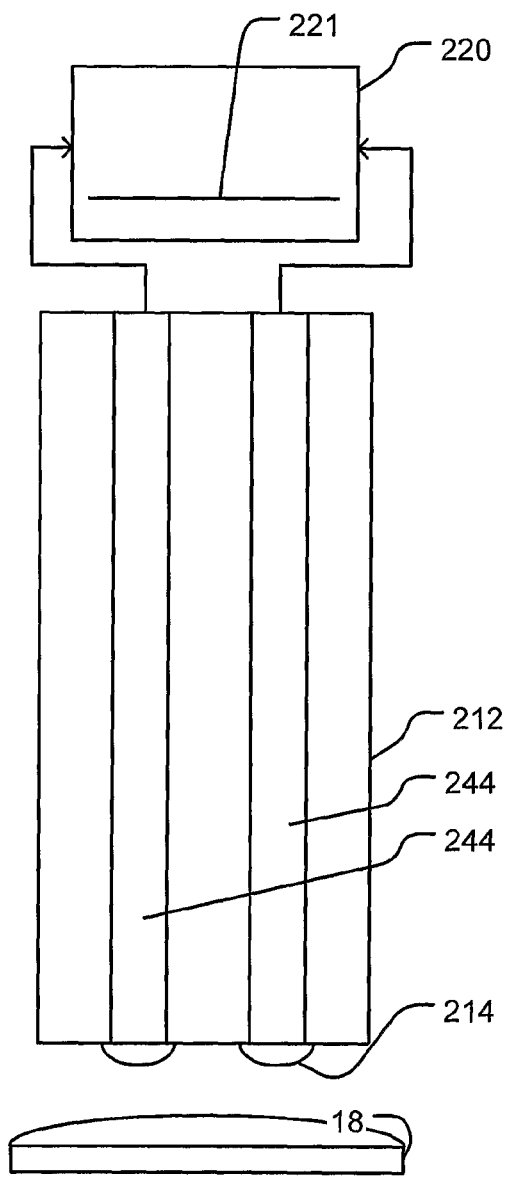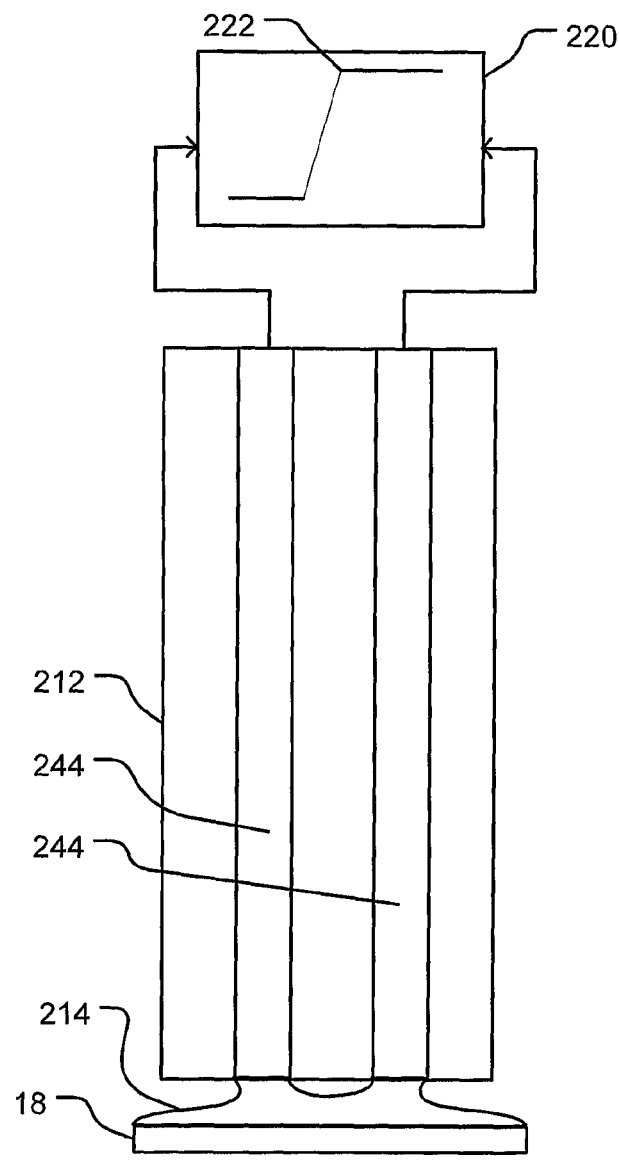
FIGURE 14
FIGURE 15

REAGENT DELIVERY APPARATUS AND METHODS

REFERENCE TO RELATED APPLICATION

This application claims priority from U.S. patent application No. 60/577,928 filed on 9 Jun. 2004 and entitled REAGENT DELIVERY DEVICE which is hereby incorporated herein by reference. For the purpose of the United States of America, this application claims the benefit under 35 U.S.C. §119 of U.S. patent application No. 60/577,928 filed on 9 Jun. 2004.

TECHNICAL FIELD

This invention relates to the delivery of reagents to specimens. For example, the invention has application to applying reagents to arrayed samples such as microarrays.

BACKGROUND

Some medical tests involve staining individual samples. The samples may be, for example, small pieces of tissue obtained from a subject by way of a biopsy. It is tedious and time consuming to manually stain individual samples. Manually staining individual samples also introduces the possibility of errors.

Conventional staining protocols involve batch staining by incubating volumes of pre-treatment reagent and primary reagents over an array of samples arranged on a slide. The reagents may include antibodies, immunohistochemical staining materials, other markers, or the like. Relatively large volumes of reagents can be required to ensure that all of the samples on a slide are appropriately treated. Reagents can be expensive. Consequently, batch staining is costly and can also compromise the accuracy of results. In addition, batch staining generally requires all of the samples on a slide to be treated with the same reagent(s).

There exist various devices for automatically dispensing reagents. These devices are typically not capable of reliably dispensing sub-microliter quantities of reagent. U.S. Pat. No. 5,143,849 discloses a method for automatically positioning a dispensing tip at a desired distance from a surface onto which liquid is to be dispensed. The method features the formation on the tip of a meniscus of a nominal small volume and advancing the tip and meniscus until the surface is contacted. The resulting decrease in pressure in the tip is measured, to trigger the tip to stop its advance and to start dispensing.

Some existing apparatus for depositing reagents onto samples cannot effectively deliver reagents through liquid coverslip layers that can be used to prevent dessication of samples.

There is a need for efficient and cost effective methods and apparatus for applying reagents to samples in the medical testing field and in other fields.

SUMMARY

The following embodiments and aspects thereof are described and illustrated in conjunction with systems, tools and methods which are given as illustrative examples and are not limiting in scope.

One aspect of the invention provides apparatus for dispensing a reagent onto a sample. The apparatus comprises: a controller; a probe tip, a sensor and an actuator. The sensor is for detecting adhesion of a droplet of reagent on the probe tip. The sensor communicates with the controller. The actuator is coupled to the probe tip and operative to advance the probe tip toward a sample and retract the probe tip from the sample under control of the controller. The controller includes a logic mechanism that causes the controller to: advance the probe tip toward the sample until the sensor detects an alteration in an adhesion of the droplet to the probe tip; and, withdraw the probe tip from the sample in response to the detection of an alteration in an adhesion of the droplet to the probe tip.

Another aspect of the invention provides a method for depositing a reagent onto a sample. The method comprises forming a droplet of the reagent on a probe tip; placing the probe tip near the sample; advancing the probe tip toward the sample and monitoring for an alteration in adhesion of the droplet to the probe tip; allowing the droplet to contact the sample and thereby altering an adhesion of the droplet to the probe tip; and, upon detecting the alteration in adhesion of the droplet to the probe tip, withdrawing the probe tip from the sample.

Another aspect of the invention provides a method for depositing a reagent onto a sample. The method comprises: forming at least one droplet of the reagent on a probe tip comprising first and second electrodes; placing the probe tip near the sample; advancing the probe tip toward the sample and monitoring electrical conductivity between the first and second electrodes; and, upon detecting an alteration in the electrical conductivity between the first and second electrodes, halting advance of the probe tip toward the sample.

Another aspect of the invention provides a probe tip for delivering sub-microliter droplets of reagent to samples, the probe tip has an end surface for holding a droplet of a reagent, a plurality of hydrophilic areas on the end surface and a hydrophobic area between the hydrophilic areas.

Further aspects of the invention and features of various embodiments of the invention are described below and/or shown in the appended drawings.

BRIEF DESCRIPTION OF THE DRAWINGS

Example embodiments are illustrated in the appended drawings. The embodiments shown in the drawings are illustrative rather than restrictive.

FIGS. 7A, 7B and 7C are respectively a cross section view of a probe tip having an optical droplet detecting mechanism; an end view of a possible configuration of hydrophilic areas on an end of a probe tip; and a schematic view of a probe tip equipped with a vibration-based droplet detection mechanism;

FIGS. 14 and 15 are schematic views illustrating an alternative non-contact mechanism for detecting the delivery of reagent to a sample.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Small quantities of reagent can be transported to and deposited onto a sample by adhering a droplet of reagent on a probe tip and placing the probe tip near to the sample. If the sample has a sufficient affinity for the reagent then some or all of the reagent will remain on the sample when the probe tip is withdrawn. It is not necessary for the probe tip to contact the sample.

Figure 1:
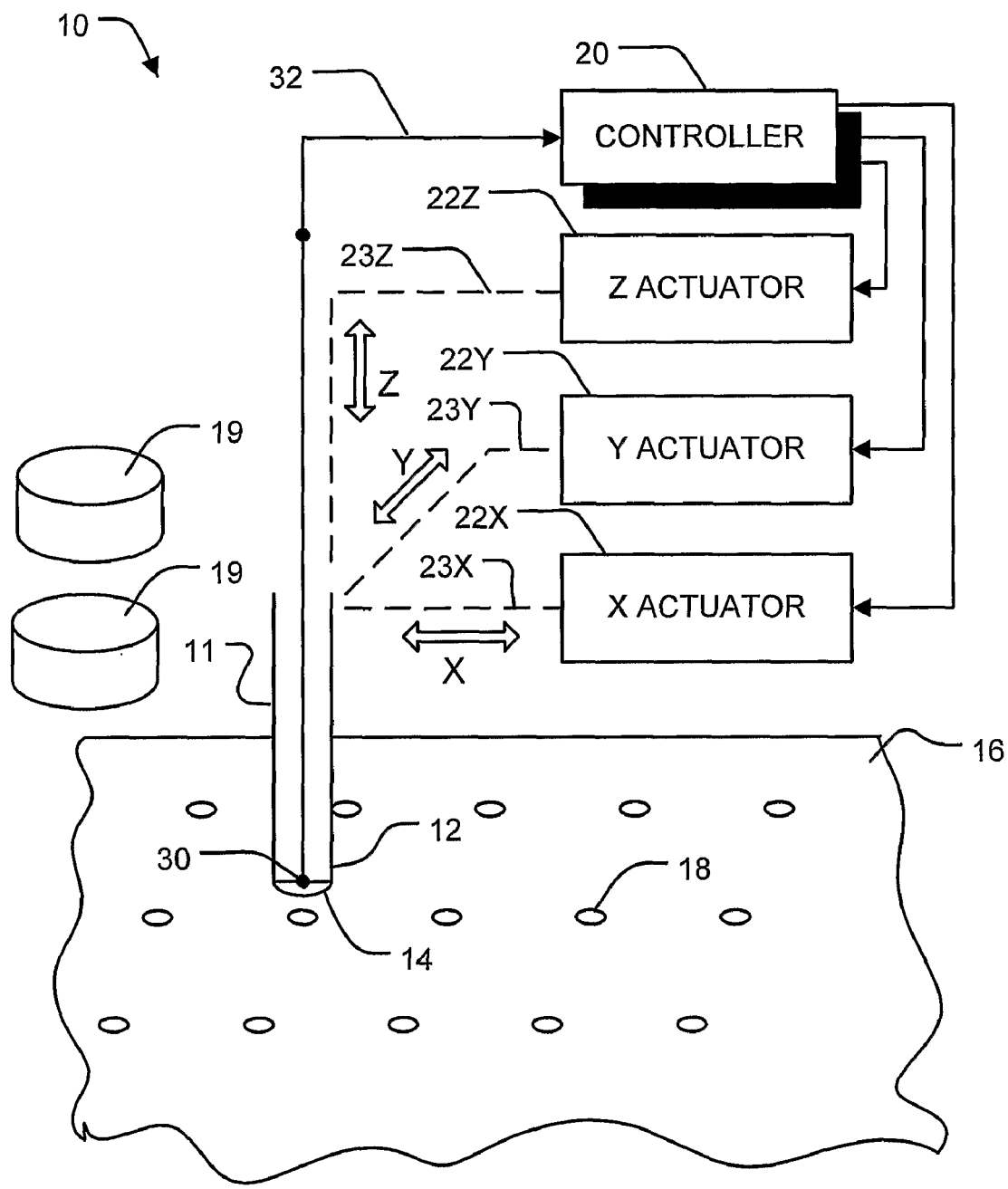
FIG. 1 is a schematic view of apparatus for applying reagents to samples on a tissue microarray slide.

FIG. 1 is a conceptual schematic view of apparatus 10 that includes a probe 11 having a tip 12 for delivering reagents to a sample. A droplet 14 of a reagent is shown adhering to probe tip 12. FIG. 1 is not to scale. A position control system is provided to move probe tip 12 relative to a slide 16 carrying an array of samples 18 to be treated with one or more reagents. Slide 16 may be made of glass or some other suitable material. Wells 19 containing reagents are located near slide 16.

The motion control system comprises a controller 20 that controls actuators 22X, 22Y and 22Z (collectively actuators 22). Actuators 22 may comprise linear actuators, stepper motors, servo motors or the like. Controller 20 includes drivers suitable for controlling the operation of actuators 22. Actuators 22X, 22Y and 22Z are respectively coupled to probe 11 by linkages 23X, 23Y and 23Z to permit movement of probe tip 12 along X, Y and Z axes. Any suitable mechanisms may be used to control the position of probe tip 12 relative to slide 16. A wide variety of such mechanisms are known. Controller 20 may receive feedback regarding the position of probe tip 12 from position sensors (not shown) or may operate in an open loop mode.

Controller 20 may comprise one or more data processors executing suitable software, suitable hardware logic circuits or both. In some embodiments, controller 20 comprises a CPU, such as a CPU in a programmable controller or a computer running software such as, for example, a Labview™ program.

It is convenient but not mandatory that the X and Y axes be orthogonal to one another. All that is necessary is that controller 20 be able to guide probe tip 12 to a location adjacent a desired sample 18. X and Y actuators 22X and 22Y could be coupled to move slide 16 relative to probe tip 12. Positioning mechanisms such as rotary tables, sliding tables, linear actuators, rotary actuators or the like could be provided to bring probe tip 12 and a desired sample 18 adjacent to one another such that probe tip 12 can be advanced toward the sample 18 under the control of controller 20.

Controller 20 includes logic that can be configured to control actuators 22 to dip probe tip 12 into a container 19 to pick up a droplet 14 of a reagent, move probe tip 12 until it is adjacent to a sample 18 and then advance probe tip 12 toward the sample 18 until the droplet 14 is partly or entirely pulled off from probe tip 12 by its interaction with the sample 18.

Probe tip 12 includes a detector 30 that provides a signal 32 to controller 20. Signal 32 changes when droplet 14 is partly or entirely pulled off from probe tip 12 by its interaction with the sample 18. As described below, detector 30 may be of a type that can detect the pulling off of a droplet from probe tip 12 using any of a wide variety of mechanisms. For example, detector 30 may measure any of:

- electrical conductivity;
- capacitance;
- vibration amplitude and/or amplitude of a vibrator;
- reflected light;
- other physical parameters that change when a droplet of reagent is pulled off from probe tip 12; or,
- some combination of these.

Signal 32 changes when droplet 14 is partly or entirely pulled off from probe tip 12 by its interaction with the sample 18. By monitoring signal 32, controller 20 can halt the advance of probe tip 12 toward a sample 18 before probe tip 12 contacts the sample 18 but after reagent from droplet 14 has been transferred to the sample 18.

The volume of each droplet 14 is determined by the dimensions, configuration and surface properties of probe tip 12 as well as on the surface tension and other characteristics of the reagent and the rate at which the probe tip is withdrawn from the reagent. Retracting the probe tip from the reagent quickly results in larger droplets adhering to the probe tip while retracting the probe tip from the reagent more slowly results in smaller droplets adhering to the probe tip.

It is practical to make a probe tip 12 capable of delivering very small quantities of reagent to individual samples. For example, a probe tip 12 can be designed to apply reagents in quantities of less than 1 µl. Typical designs for probe tip 12 deliver aqueous reagents in quantities in the range of 1 nl to 1 µl. It can be convenient to dimension probe tip 12 to carry droplets 14 of reagents that have volumes of about 10 nl.

Since a system 10 can deliver small quantities of reagent to each sample 18, the volume of reagent needed to treat an array of samples 18 can be lower as compared to batch staining processes. This can lower the cost of performing assays.

Figure 2:
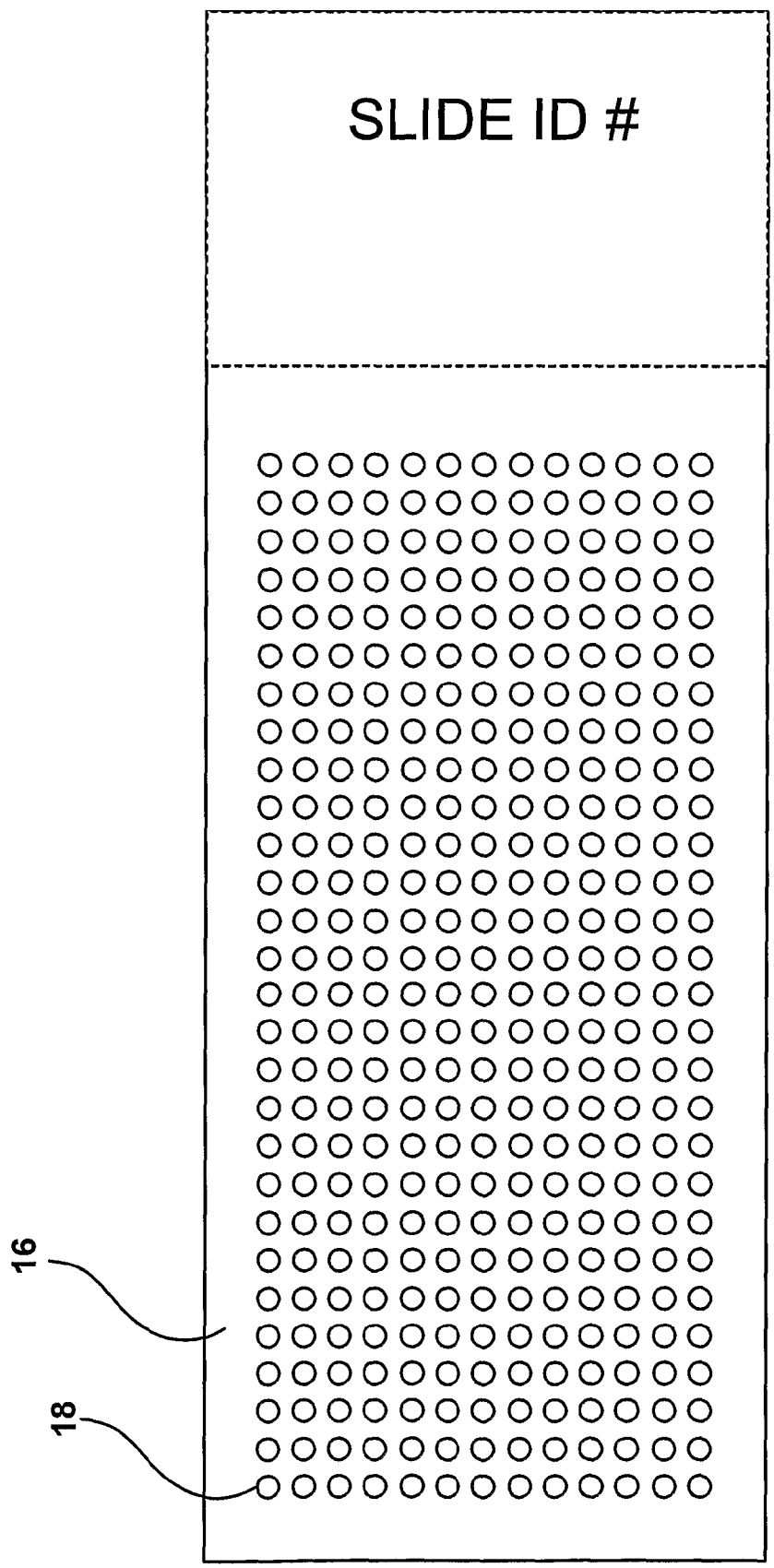
FIG. 2 is a top plan view of a tissue microarray slide.

FIG. 2 shows an example of a typical microarray slide 16. In this non-limiting example, slide 16 is a tissue microarray. Samples 18 may be, for example, approximately 2 mm apart and approximately 1 mm in diameter. Reagents can be applied to tissue samples 18 using a delivery device according to the invention.

The surface of probe tip 12 is of a material for which the reagents being used have sufficient affinity that a droplet 14 of reagent can be retained on probe tip 12 until the droplet is brought into contact with a sample 18. The reagent has, overall, a weaker affinity for probe tip 12 than for samples 18 so that upon touching a droplet 14 of reagent to a sample 18 and then withdrawing the probe tip 12, all or at least a significant part of droplet 14 is transferred from the probe tip 12 to the sample 18.

A probe tip 12 having these desired characteristics may have some areas that exhibit a relatively high affinity for the reagent and other areas that exhibit a relatively lower affinity for the reagent. For example, where the reagent is water-based, probe tip 12 may have one or more hydrophilic areas and one or more hydrophobic areas.

Figure 3:
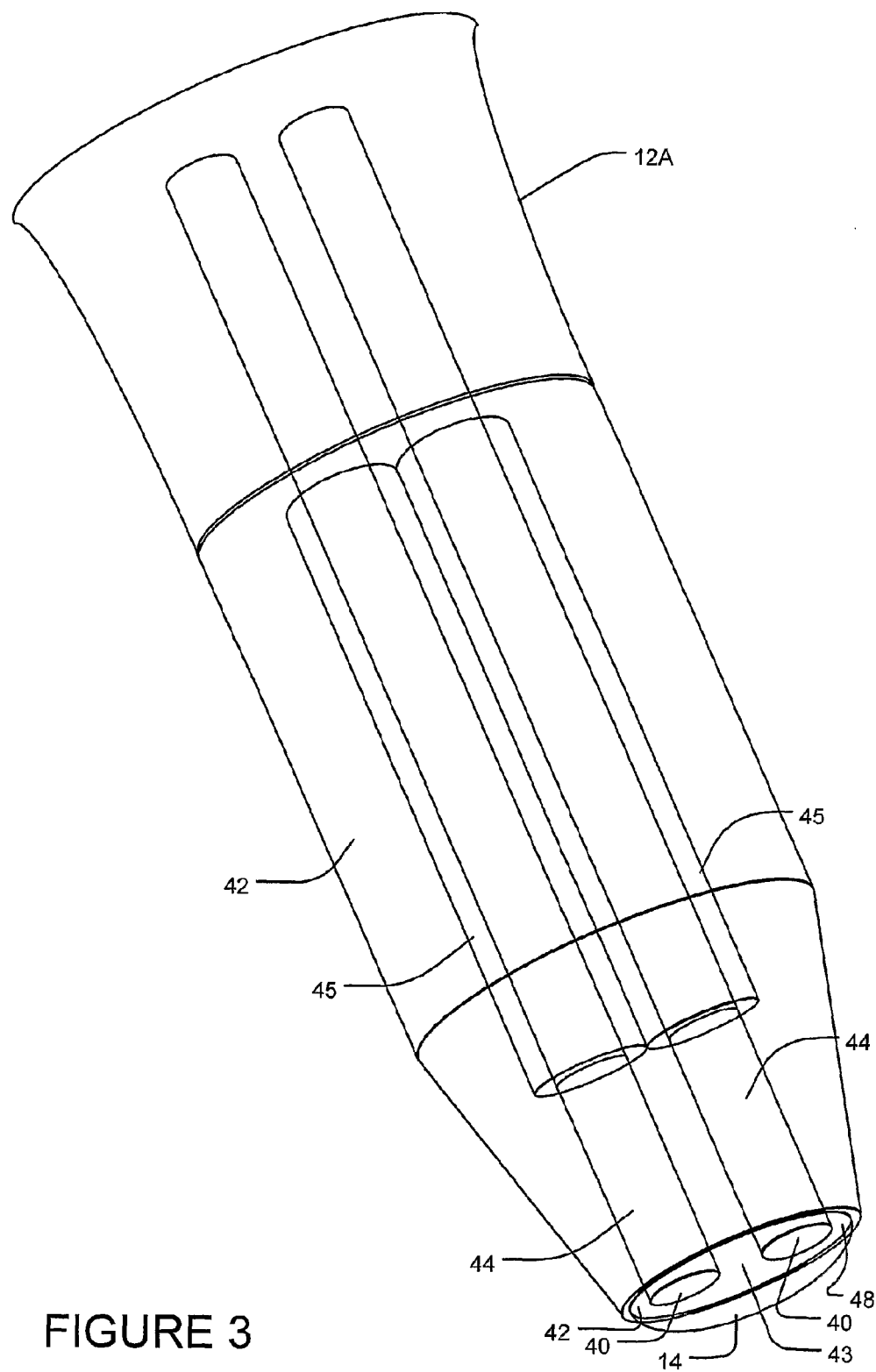
FIG. 3 is an isometric see-through view of a probe tip.
Figure 4:
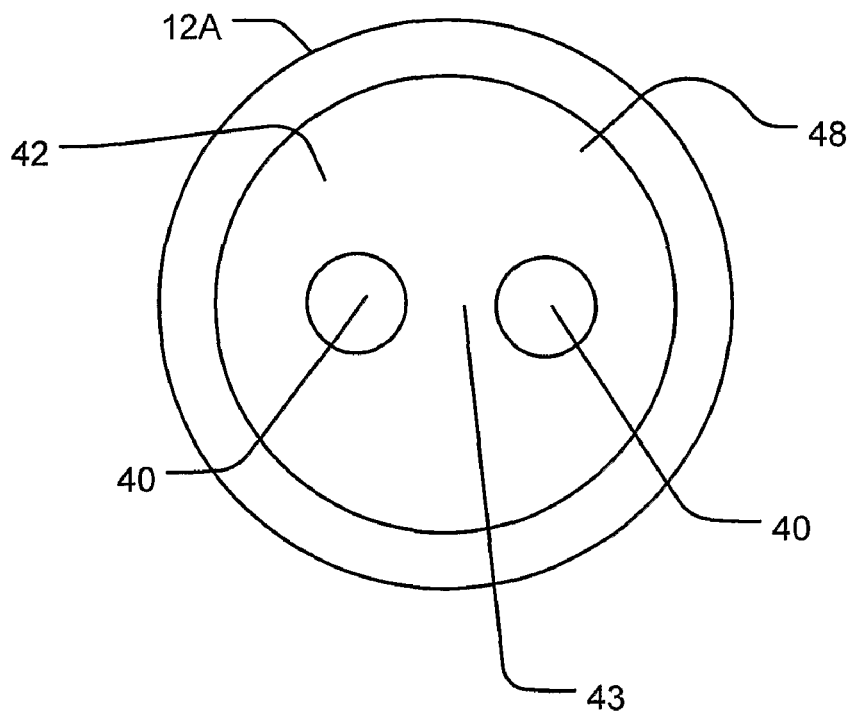
FIG. 4 is an end view of the probe tip of FIG. 3.
Figure 5:
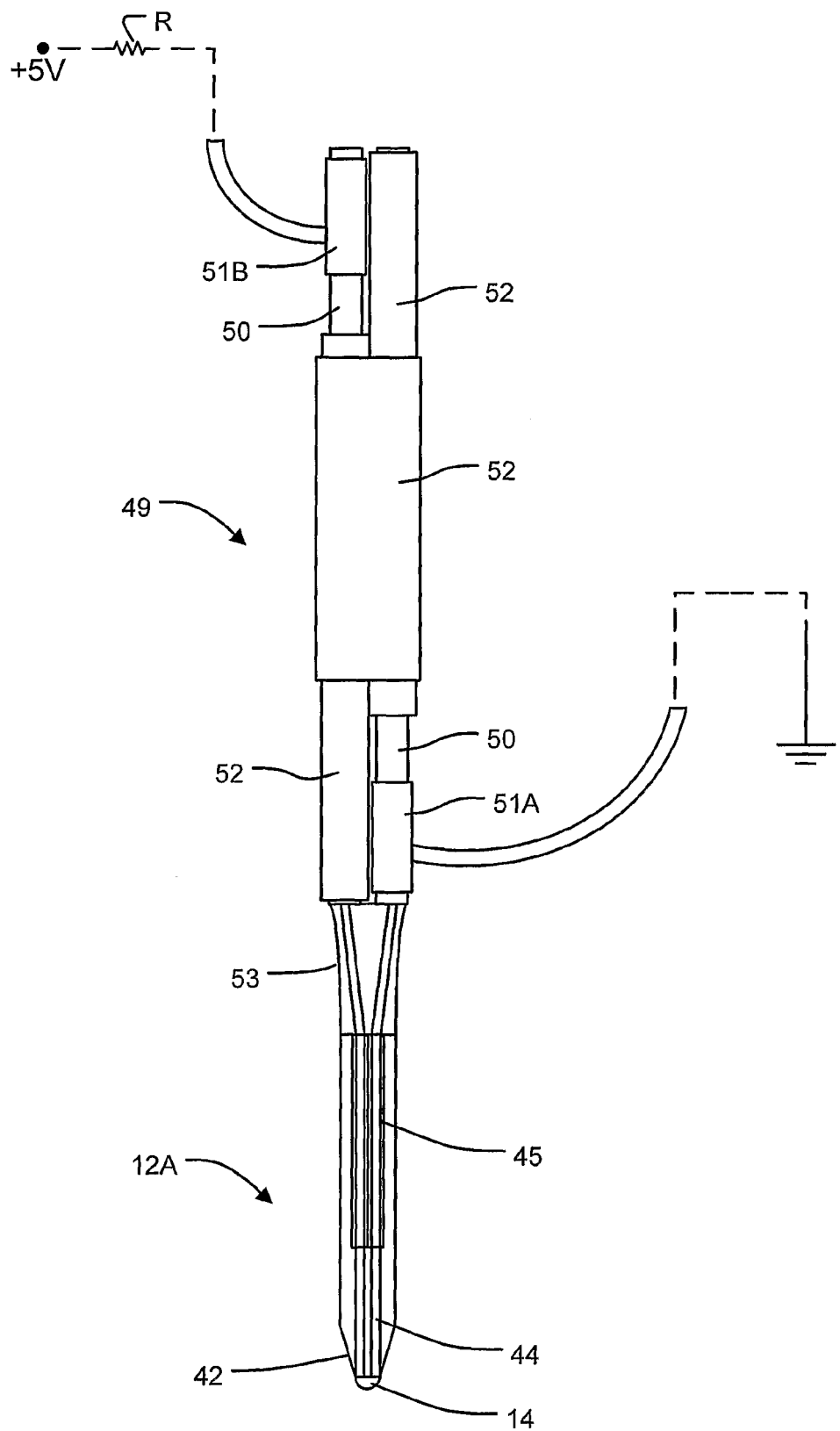
FIG. 5 is an elevation view of a probe assembly of a delivery device of a prototype design incorporating the probe tip of FIG. 3.

FIGS. 3 to 5 show a particular probe tip 12A that has hydrophilic and hydrophobic areas. Probe tip 12A comprises, a pair of relatively hydrophilic areas 40. Hydrophilic areas 40 may comprise, for example, hydrophilic metal surfaces, such as areas of stainless steel. Hydrophilic areas 40 are surrounded by a relatively hydrophobic material 42. A strip 43 of hydrophobic material separates hydrophilic areas 40.

Examples of a hydrophobic material that can be used for material 42 include PTFE (e.g. Teflon™), Parylene™, epoxide, silicone or hydrophobic plastics such as polyethylene, polypropylene or polystyrene. Hydrophobic areas may also be provided by texturing selected areas of the surface of probe tip 12A to provide dense regions of tiny pointed features such as sharp spikes that are hydrophobic because their geometry prevents wetting.

In the probe tip 12A of FIGS. 3 to 5, hydrophilic areas 40 are provided by the ends of electrodes 44. In one embodiment, each electrode 44 extends through an electrically insulating sleeve 45. Sleeves 45 prevent electrodes 44 from touching one another. Sleeves 44 may comprise, for example, tightly fitting glass sleeves.

In probe tip 12A illustrated in FIGS. 3 to 5, electrodes 44 and optional sleeves 45, pass through a body of solid, relatively hydrophobic material 42. Individuals skilled in the art will recognize that various materials are suitable for use as electrodes 44 and various other materials are suitable for use as hydrophobic material 42. The specific materials chosen are a matter of design convenience.

Probe tips for transferring reagents may have any of various suitable geometries. In the embodiment of FIGS. 3 to 5, probe tip 12A has a flat end surface 48. Tips of electrodes 44 and hydrophobic material 42 are arranged or ground flat so that the tip surfaces 40 of electrodes 44 are flush with end surface 48. In some embodiments, end surface 48 has a diameter in the range of about 0.01 mm to 5 mm. In some embodiments, end surface 48 has a diameter in the range of about ½ mm to 1 mm. In a prototype embodiment, end surface 48 has a diameter of ¾ mm.

FIG. 5 shows probe tip 12A assembled to a probe base 49 according to a prototype design. In base 49, electrodes 44 connect to larger diameter conductors 50. Electrical connections 51A and 51B connect the electrodes to a resistance measuring device. For example, electrical connection 51A may be connected to ground potential while electrical connection 51B is connected in series with a resistor to a source of electrical current having a potential of a few volts positive or negative relative to ground. In the illustrated embodiment, electrical connection 51B is connected in series with a resistor R to a source at a potential of +5 volts. Current flowing between electrodes 44 may be determined by measuring a voltage across resistor R. Other suitable means for measuring current flowing between electrodes 44 could also be provided. Probe base 49 is held together by heat-shrink tubing 52 and joined to probe tip 12A by an adhesive 53, such as a suitable epoxy.

A prototype probe tip constructed substantially as shown in FIG. 3, had the dimensions shown in Table I. This prototype probe tip was used to transfer droplets having volumes of approximately 10 nl to samples.

TABLE I

Construction of Example Prototype Probe Tip

| | |
|---|---|
| Diameter of end surface 48 (mm) | 0.75 |
| Diameter of Electrodes 44 (mm) | 0.25 |
| Spacing of electrodes 44 (mm) | 0.15 |
| Material of electrodes 44 | Stainless steel |
| Material around electrodes 44 | Teflon |

Figure 6C:
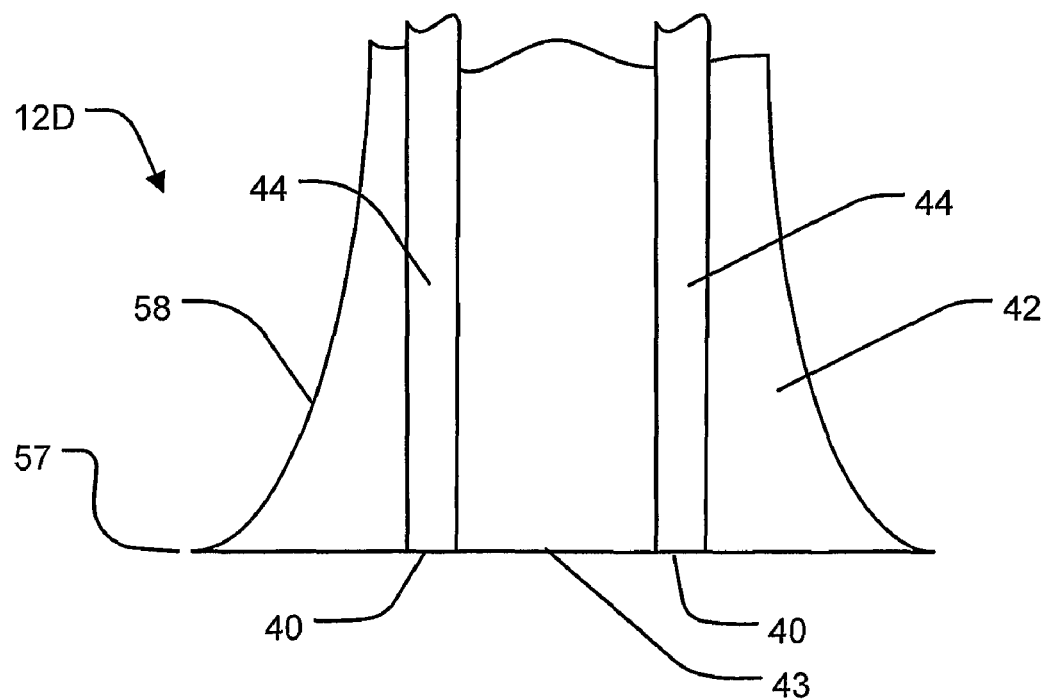
FIGS. 6A, 6B, 6C, 6D and 6E are sectional views through end portions of alternative probe tips
Figure 6A:
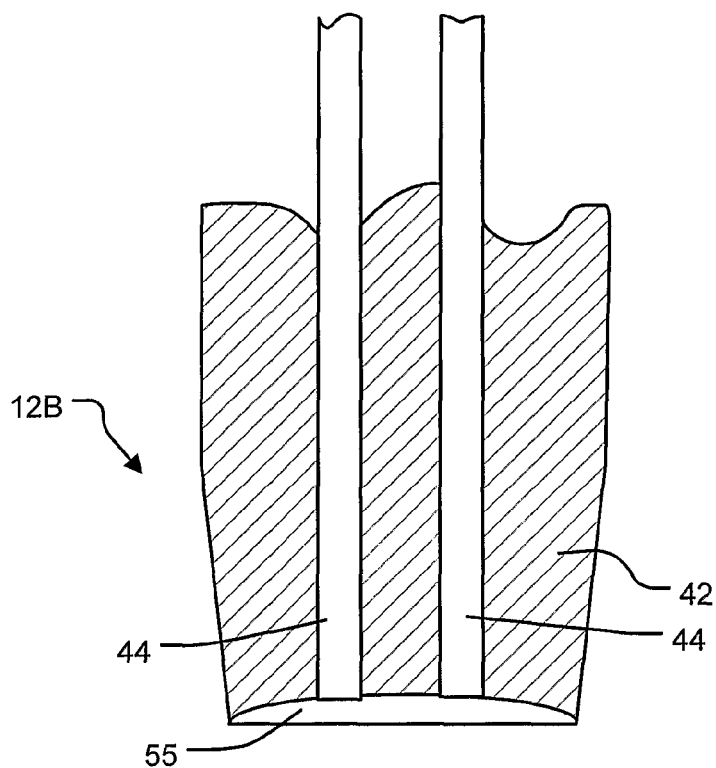
Figure 6B:
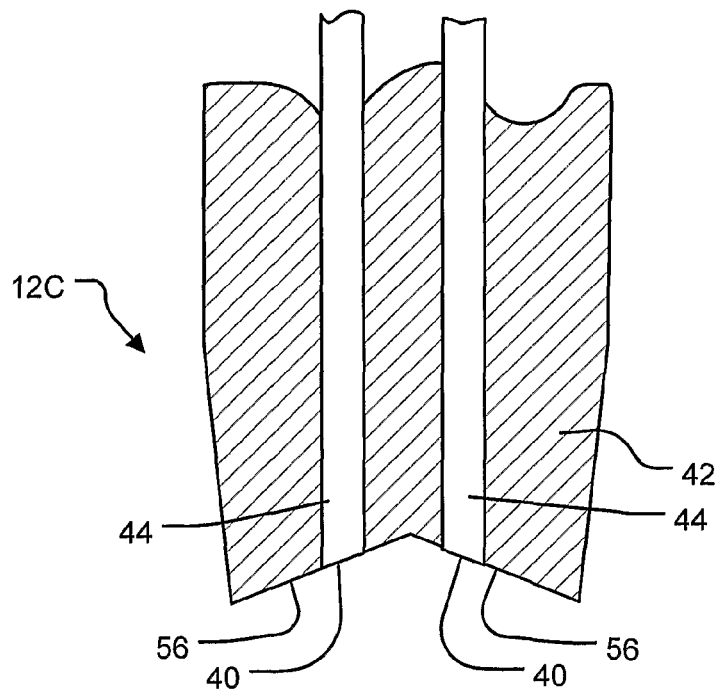
Figure 6D:
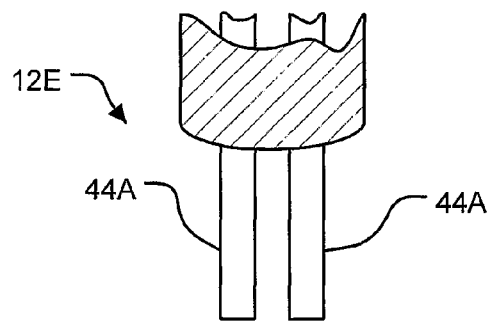
Figure 6E:
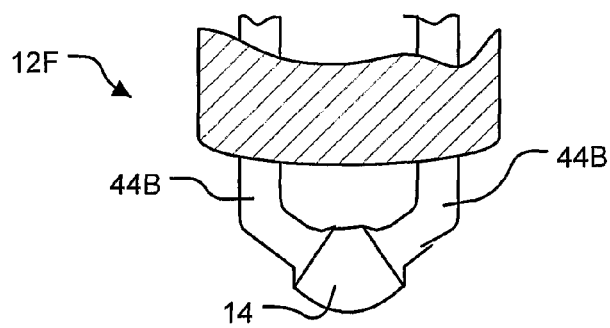

Probe tips for transferring reagents may have any of various suitable geometries. Instead of the flat-ended configuration of FIGS. 3 to 5, it is also possible for a probe tip 12 to have other configurations. For example, FIG. 6A shows a probe tip 12B having an end surface 48A that includes a concave depression 55. FIG. 6B shows a probe tip 12C having an end surface 48 configured as a dihedral. One electrode 44 is exposed to provide a hydrophilic surface 40 on each face 56 of the dihedral. FIG. 6C shows a probe tip 12D having a flat end surface 48 having an edge 57 that forms an acute angle with side surfaces 58 of probe tip 12D. FIG. 6D shows a probe tip 12E comprising a pair of spaced-apart electrodes 44A having hydrophilic end faces and separated by an air gap 59. In the illustrated embodiment, the end faces of electrodes 44A are, flat and in the same plane. Other configurations are possible, for example, FIG. 6E shows a probe tip 12F having electrodes 44B. The end surfaces of electrodes 44B are angled toward one another. As also illustrated in FIG. 6E the end surface of each electrode may have an edge that forms an acute angle with side surfaces of the electrode. A probe tip may permit the spacing between electrodes 44B to be varied and/or permit the angle of electrodes 44B relative to one another to be varied. Any suitable adjustment mechanism may be provided.

Figure 6F:
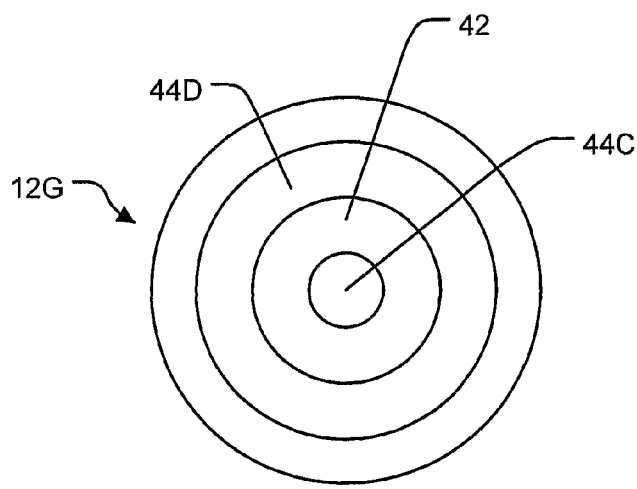
FIG. 6F is an end view of another alternative probe tip.

FIG. 6F is an end view of a probe tip 12G having first and second coaxial electrodes. A central electrode 44C is within and concentric with an annular outer electrode 44D. An annular region of a hydrophobic material lies between the electrodes.

Various mechanisms may be provided to detect the adhesion of a droplet to a probe tip. Probe tip 12A of FIGS. 3 to 5 uses hydrophilic areas 40 as electrodes to sense the presence of a droplet 14 of reagent. This may be done by measuring an electrical current passing between electrodes 44. In the illustrated embodiment, an electrical source is connected between electrodes 44 and an electrical current flowing in one or both of electrodes 44 is measured. In the absence of a droplet 14 of reagent on the end of probe tip 12 electrodes 44 are electrically well insulated from one another and the electrical current is small or zero. When a droplet 14 is present on the end of probe tip 12A, an electrical connection is created between the two electrodes 44 so that a measurable electric current flows in at least one of electrodes 44.

Other mechanisms for detecting the presence of a droplet of reagent adhering to a probe tip 12 may also be provided. For example, FIG. 7A shows a probe tip 12E which includes an optical fiber 60 that terminates at a window 62 on an end 64 of probe tip 12E. A light source 66 delivers optical radiation through a beam splitter 67 into optical fiber 60. A light detector 68 monitors optical radiation reflected at window 62. The nature of the reflected radiation will depend upon whether or not a droplet 14 of reagent is present on the end 64 of probe tip 12E.

Window 62 may be made partly or entirely hydrophilic. In the alternative, window 62 may be made hydrophobic and may be located between hydrophilic areas 40 as shown in FIG. 7B. Hydrophilic areas 40 may be patterned onto the end of probe tip 12E or may be exposed parts of bodies of hydrophobic material embedded in the end of probe tip 12E. Hydrophilic areas 40 may be provided in the form of one or more annular regions surrounding window 62.

Figure 7C:
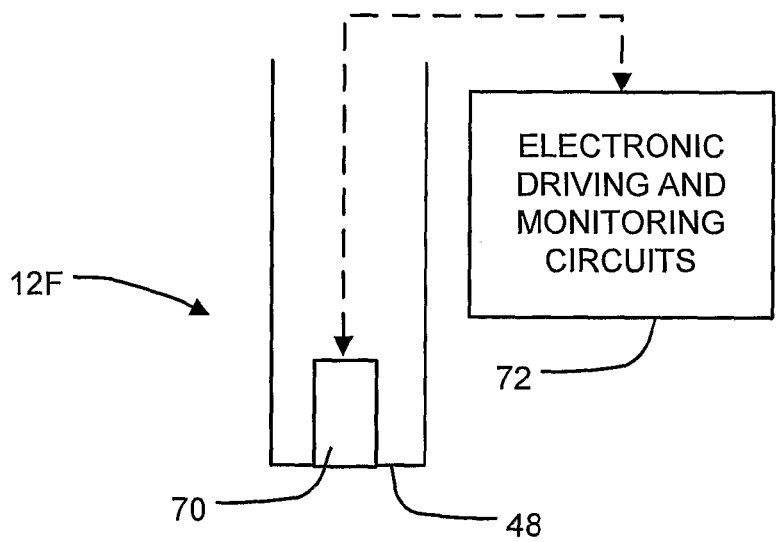

FIG. 7C shows a probe tip 12F that incorporates another mechanism for detecting the presence of a droplet of reagent on the end of probe tip 12F. Probe tip 12F includes a vibrator 70 such as a small piezoelectric element. The frequency of vibration of vibrator 70 depends upon whether or not a droplet of reagent is adherent at the end 48 of probe tip 12F. An electronic driving circuit 72 drives vibrator 70 and monitors its frequency of vibration. In some embodiments, the surface of probe tip 12F near vibrator 70 is hydrophilic. In other embodiments, hydrophobic the surface of probe tip 12F near vibrator 70 is hydrophobic and is located between two or more hydrophilic areas on probe tip 12F.

Figure 8:
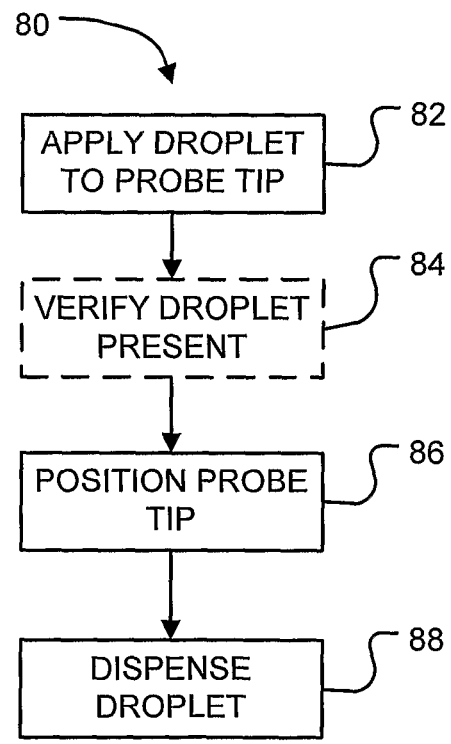
FIG. 8 is a flow chart illustrating a method for dispensing a reagent onto a sample.

The ability to detect detachment of a droplet of reagent from the end of a probe tip 12 permits droplets of reagent to be applied to samples without having the probe tip contact the samples. FIG. 8 illustrates one method 80 for applying a reagent to a sample. In block 82 a droplet of reagent is applied to the end of a probe tip 12. Block 82 may involve, for example, dipping the probe tip 12 into an appropriate reagent. A small droplet of the reagent adheres to the end of the probe tip when the probe tip is withdrawn from the reagent. In some embodiments, wells or other containers each containing a quantity of a reagent are located at positions known to a controller 20 (see FIG. 1 for example). Controller 20 operates X-axis and Y-axis actuators 22X and 22Y to position probe tip 12 over a container holding a desired reagent and then operates Z-axis actuator 22Z to advance probe tip 12 into the reagent and then to withdraw probe tip 12.

In optional block 84, controller 20 uses a droplet detection mechanism to verify that a droplet of reagent is present on the end of probe tip 12. For example, where the probe tip 12 is a probe tip 12A as shown in FIG. 3, controller 20 may measure a signal indicative of the electrical resistance between electrodes 44 and may proceed if the electrical resistance is lower than a threshold value.

In block 86 probe tip 12 is positioned over a sample to which the reagent is to be applied. Block 86 typically comprises controller 20 using coordinates of the sample in a suitable coordinate system and operating X-axis and Y-axis actuators 22X and 22Y to position probe tip 12 over the sample.

The droplet is dispensed in block 88. To dispense the droplet onto a sample, probe tip 12 is advanced toward the sample until the droplet 14 of reagent comes into contact with the sample. FIG. 9 shows a probe tip 12 having a droplet 14 touching a sample 18. The droplet has an affinity from the sample and is attached to and/or absorbed into the sample 18. Sample 18 may be, for example:
  a tissue biopsy,
  a mass of cells from an animal, plant, bacteria or person, or the like,
  a composition including viruses,
  a single cell from an animal, plant bacteria or person, or the like,
  a deposit of biological material such as DNA or RNA, or
  a material comprising DNA or RNA.
The interaction between the droplet 14 and sample 18 is such that the droplet at least sticks to sample 18.

In FIG. 9, samples 18 are shown as being covered by a layer 19 of a liquid coverslip material. A liquid coverslip may be applied to prevent samples 18 from drying out and/or to guard against any fluid crosstalk between different samples 18. Layer 19 may comprise a hydrophobic layer (for example a layer of a hydrocarbon-based liquid coverslip). Layer 19 provides a fluidic boundary between samples 18. Layer 19 may be, for example, 2-5 mm in thickness.

In some cases droplet 14 absorbed by the sample after it comes into contact with the sample and is consequently pulled away from the end of probe tip 12. In such cases, controller 20 can determine that droplet 14 has come into contact with sample 18 when detector 30 detects that droplet 14 has been pulled away from the end of probe tip 12. In such cases block 88 may comprise advancing the probe tip toward the sample and halting the advance when detector 30 detects that droplet 14 has been pulled away from the end of probe tip 12.

Figure 9A:
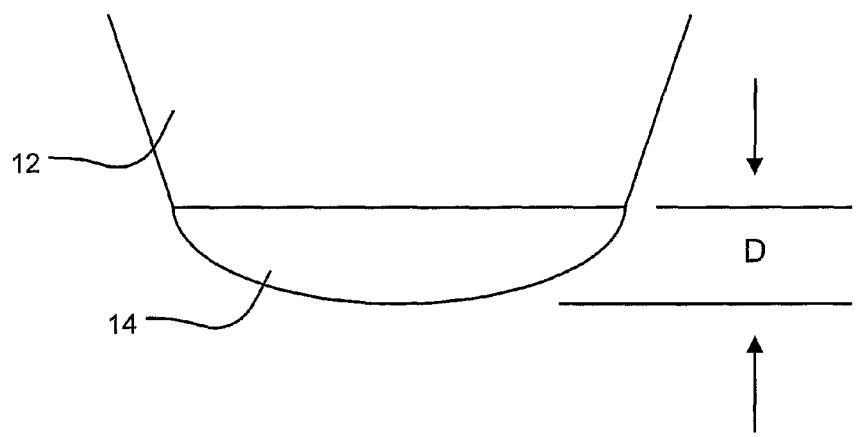
FIG. 9A is an enlarged view of a probe tip.
Figure 9:
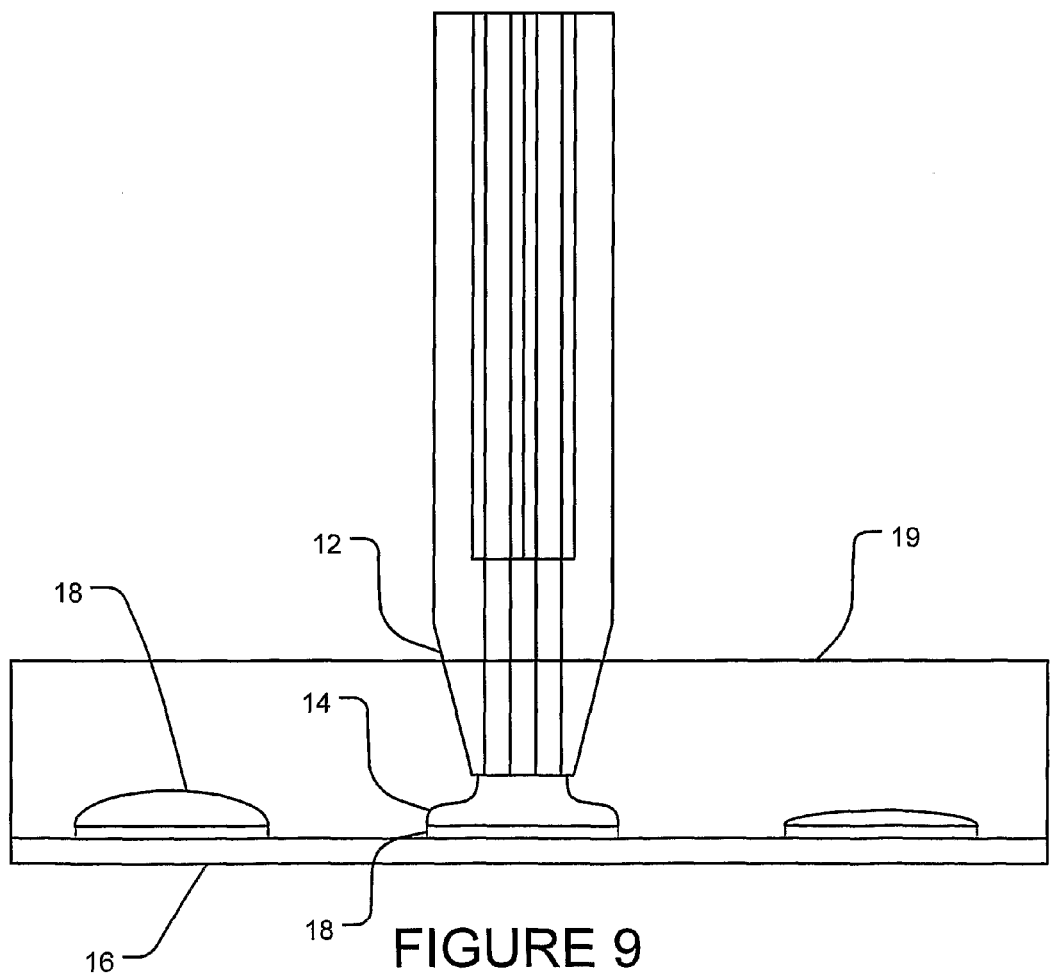
FIG. 9 is an elevation view showing a droplet of reagent being applied to a sample by a probe tip.

A droplet 14 not in contact with a sample 18 projects from the end surface 48 of probe tip 12 by an amount D (see FIG. 9A). The droplet thickness, D is determined primarily by the physical dimensions of end surface 48, the nature of the interaction between the reagent, the material(s) of end surface 48, and the nature of the medium surrounding droplet 14. In a number of the embodiments described above, droplet 14 is attracted to two or more hydrophilic areas 40 and bridges a hydrophobic area 43 between the hydrophilic areas. Where droplet 14 bridges a hydrophobic area, the energy of the droplet 14 is increased. This tends to make it easier for droplet 14 to be pulled off of a probe tip 12 when the droplet comes into contact with a sample 18.

In some embodiments, block 88 comprises serially advancing probe tip 12 toward sample 18 by increments $\Delta Z$ that are smaller than D and then checking detector 30 to determine whether or not droplet 14 has been pulled away from the end of probe tip 12 after each incremental advance. If droplet 14 has been pulled away from the end of probe tip 12 then controller 20 halts the advance. If not, controller 20 advances probe tip 12 by another increment $\Delta Z$. Preferably $\Delta Z$ is significantly less than D, and is preferably less than $\frac{1}{2}$D.

In other embodiments, probe tip 12 is advanced toward sample 18 in small discrete steps. Each step moves probe tip 12 closer to sample 18 by a distance increment $\Delta Z^+$. After each step, probe tip 12 is retracted by a distance increment $\Delta Z^-$ and detector 30 is checked to determine whether or not droplet 14 has been pulled away from the end of probe tip 12. In such embodiments, $\Delta Z^+$ can be larger than D as long as $\Delta Z^+ - \Delta Z^-$ is smaller than D. Preferably $\Delta Z^+ - \Delta Z^-$ is less than $\frac{1}{2}$D or $\frac{1}{4}$D. In some embodiments, $\Delta Z^+ - \Delta Z^-$ is about 10% of D or less. In some embodiments, $\Delta Z^+ - \Delta Z^-$ is on the order of about 100 μm.

Figure 10:
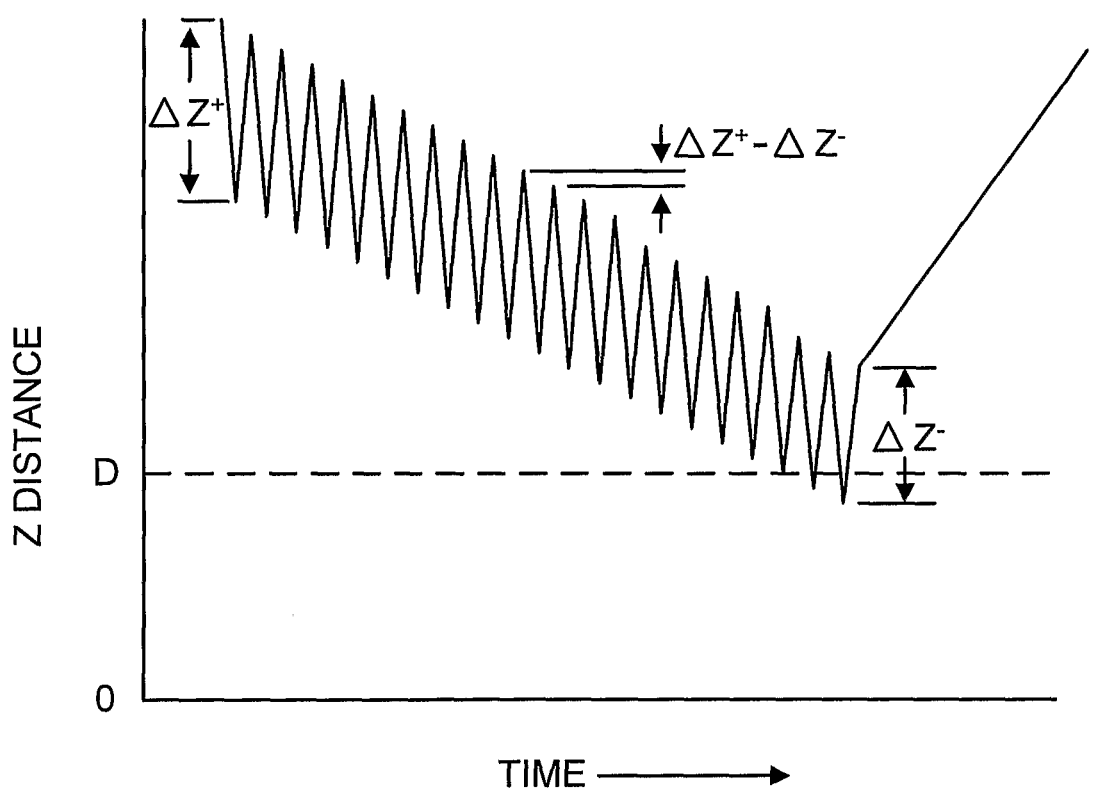
FIG. 10 is a plot illustrating an approach of a probe tip to a sample.

FIG. 10 illustrates a possible trajectory of a probe tip 12. The vertical axis illustrates the distance from the end of probe tip 12 to a sample 18. The horizontal axis indicates time. Probe tip 12 is initially positioned a safe distance above sample 18. Then probe tip is advanced by a distance $\Delta Z^+$ and retracted by the distance $\Delta Z^-$. Since $\Delta Z^+ > \Delta Z^-$ the net result of this motion is that the probe tip moves closer to the sample by a distance $\Delta Z^+ - \Delta Z^-$. After each retraction, controller 20 checks to determine if electrical contact is still present between the electrodes. When the electrical connection is lost, it is known that droplet 14 has been pulled off from the end of probe tip 12. The probe tip is then retracted. As long as the controller 20 detects that the drop has been pulled off from probe tip 12 before probe tip 12 touches sample 18, the probe tip is prevented from ever coming into contact with the sample 18.

A dispensing apparatus may incorporate a mechanism to prevent damage to a probe tip 12 in case the probe tip 12 is driven into a slide 16 due to some failure. Any one or more of a wide variety of such safety mechanisms may be provided. For example, a force sensor may be provided to detect forces applied to the probe tip. Controller 20 may be configured to monitor an output of the force sensor and to stop moving the probe tip if excessive forces are detected.

Figure 11:
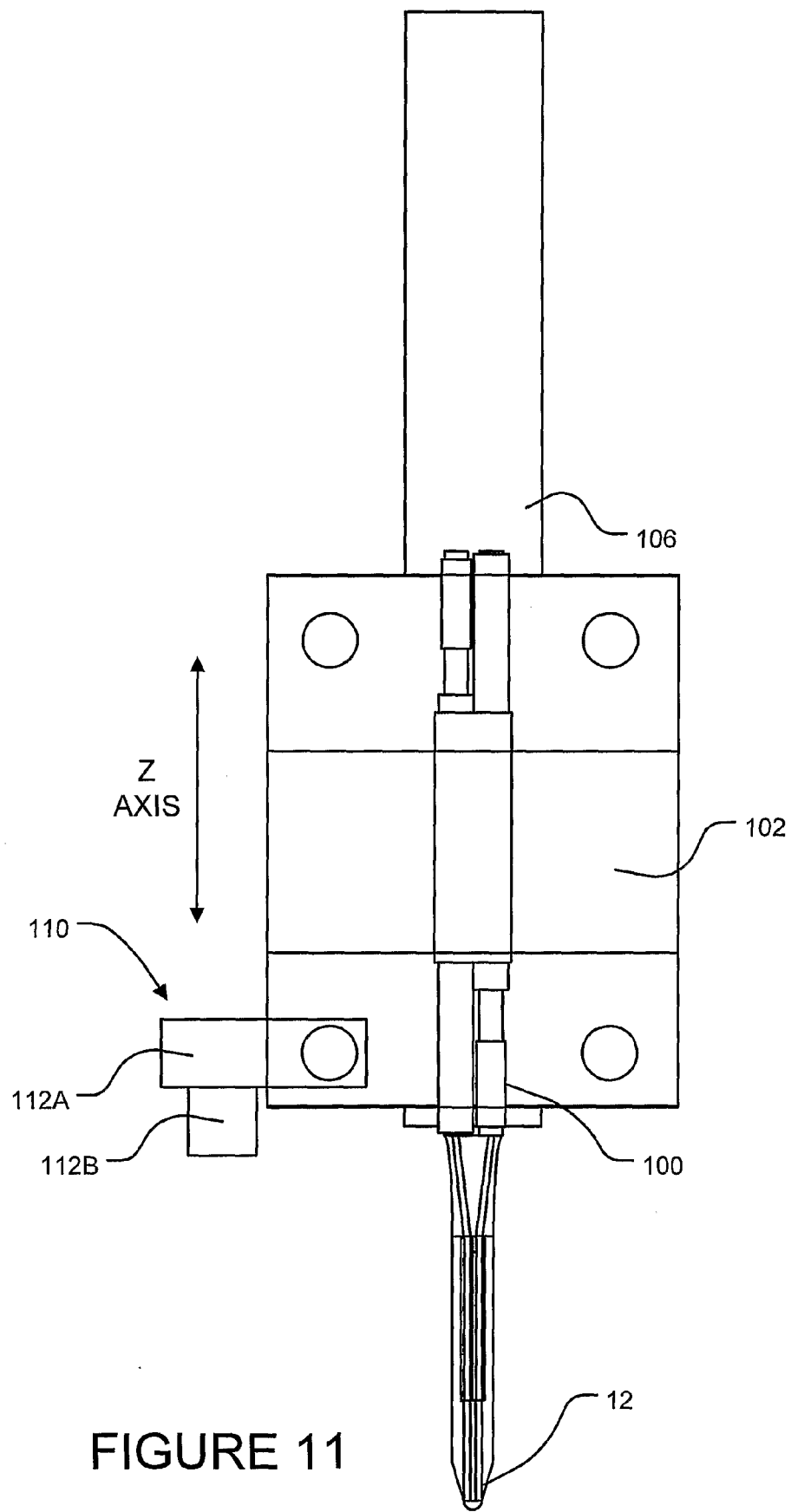
FIG. 11 is an elevation view of a system for mounting a probe tip that includes a safety mechanism.

Another safety mechanism shown in FIG. 11 mounts an assembly 100 carrying probe tip 12 on a sliding mount 102. Sliding mount 102 can slide vertically. In the illustrated embodiment, sliding mount 102 comprises a collar comprising low-friction rollers (not shown) that engage a vertically-extending rail 106. Z axis actuator 22Z (not shown in FIG. 11) is connected to move rail 106 vertically.

Normally the weight of probe tip assembly 100 and sliding mount 102 keeps probe tip 12 in a lowermost position against an end stop (not shown). If Z axis actuator 22Z attempts to drive the end of probe tip 12 into a rigid surface, such as slide 16, sliding mount 102 moves upward on rail 106, thereby preventing probe tip 12 from being driven into the surface.

The force on the end of probe tip 12 is essentially limited to the weight of probe tip assembly 100 and sliding mount 102.

A detector 110 detects vertical motion of sliding mount 102. Operation of Z axis actuator 22Z in a direction toward the slide 16 is inhibited in response to detector 110 detecting motion of sliding mount 102. In a simple embodiment, motion of sliding mount 102 opens an electrical connection between an electrode 112A mounted to sliding mount 102 and another electrode 112B that is fixed in the Z-axis direction. When this electrical connection is broken, motion of probe tip 12 in a downward direction is immediately stopped.

Figure 12:
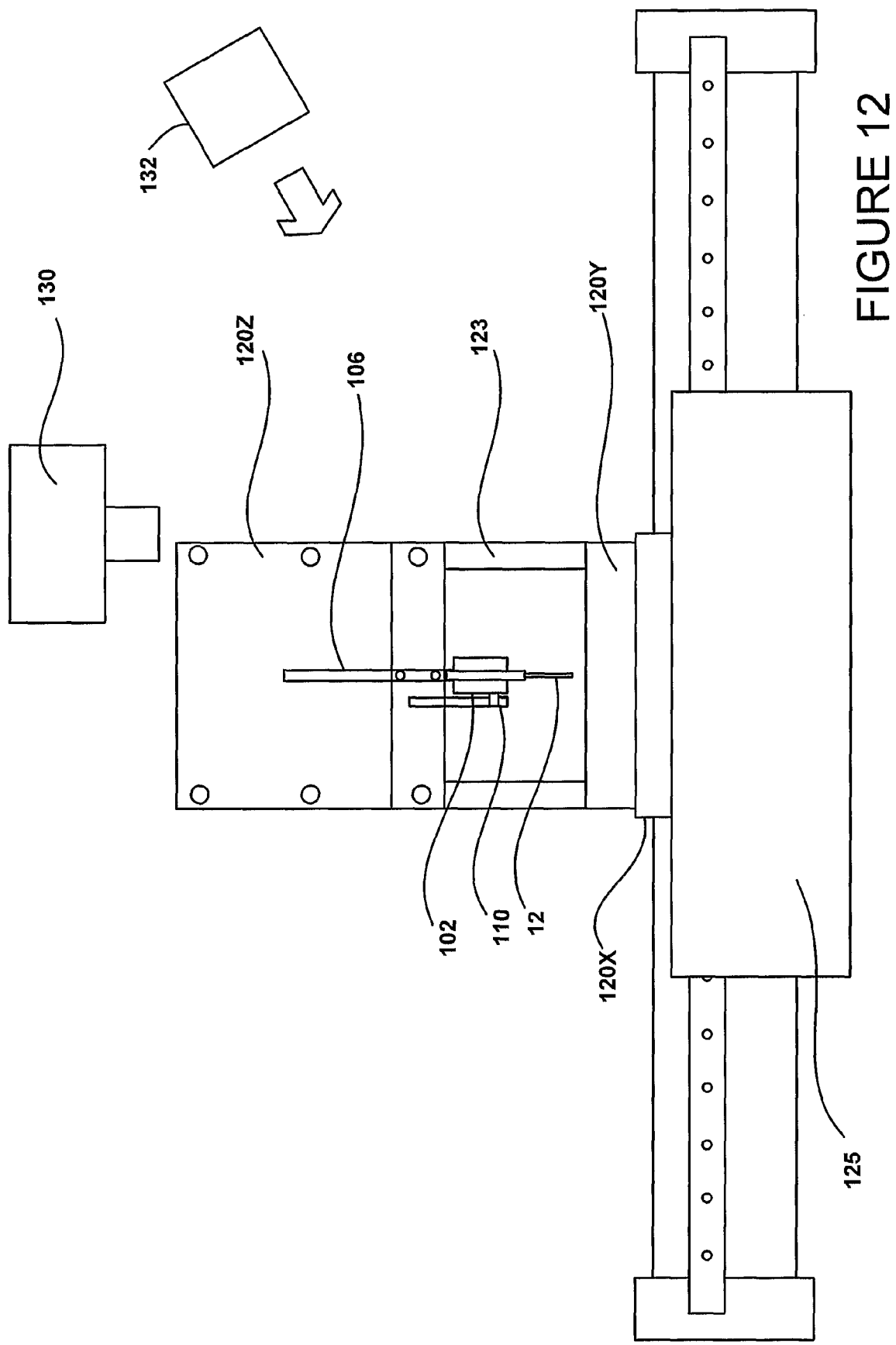
FIGS. 12 and 13 are schematic front and top views of a prototype apparatus for delivering droplets of reagent to samples.
Figure 13:
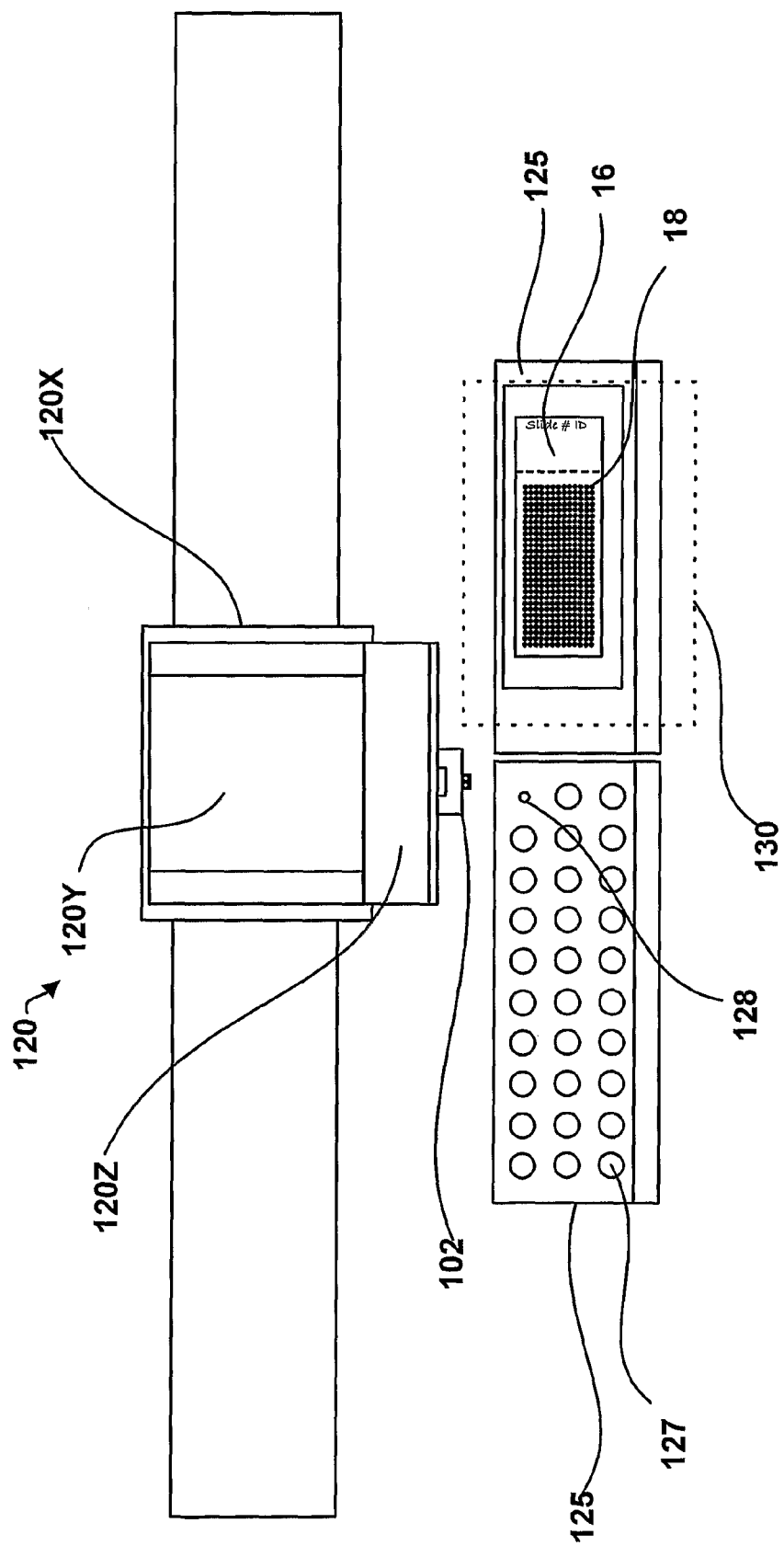

FIGS. 12 and 13 are schematic front and top views of a prototype apparatus for delivering droplets of reagent to samples. In this prototype, a probe tip 12 is carried on a three-axis positioner 120 made up of an X-axis stage 120X that carries a Y-axis stage 120Y. A Z-axis stage 120Z is mounted to Y-axis stage 120Y by supports 123. The stages of positioner 120 include suitable actuators that can be controlled by a controller (not shown in FIG. 12 or 13) to move probe tip 12 in three orthogonal directions.

A fixture 125 is mounted in front of positioner 120. Fixture 125 holds one or more slides 16 and supplies of reagents. In the illustrated embodiment, fixture 125 has a number of wells 127 for holding reagents.

It can be desirable to provide a mechanism for cleaning probe tip 12. A cleaning procedure may be performed between spotting reagents onto samples to remove any liquid coverslip or any reagent that might still be adhering to probe tip 12. A cleaning procedure may, for example, involve dipping probe tip 12 into a suitable solvent and then delivering a short blast of air to probe tip 12. The air blast removes any solvent from the probe tip. Any suitable solvent may be used. Solvents that may be appropriate for certain applications include but are not limited to: aromatic or aliphatic hydrocarbons, xylene, ethanol, methanol and combinations thereof.

In an example embodiment of the invention, after delivering a spot of a reagent to a sample 18, controller 20 automatically moves probe tip 12 to a location over a container of a suitable solvent, advances probe tip 12 into the solvent, retracts probe tip 12, moves probe tip 12 to a location over an orifice, and opens a valve to cause a blast of air to be delivered through the orifice. The cleaned probe tip 12 is then moved to a location to collect a droplet of reagent for the next sample 18. Optionally the cleaning cycle may involve sequentially dipping probe tip 12 into two or more solvent baths.

Fixture 125 may include a cleaning station comprising one or more reservoirs containing solvents or other cleaning materials and/or an air blast orifice. FIG. 13 shows a fixture 125 having an air blast orifice 128. Solvents may be provided in one or more of wells 127.

For controller 20 to move probe tip 12 to a location corresponding to a particular sample, controller 20 must have available information defining a the location of the sample. This information may be made available to controller 20 in any of a number of ways. The following are some examples of such ways:

Controller 20 may control the initial placement of samples 18 on slide 16. For example, samples 18 may be placed using probe tip 12 or a suitable manipulation device mounted in place of probe tip 12.

Samples 18 may be placed at predefined locations on slide 16. The predefined locations are defined relative to reference features on slide 16, such as edges of slide 16. Apparatus 10 may include pins or other registration members so that each slide 16 can be repeatably mounted with its registration features at known locations in a coordinate system used by apparatus 10. In the embodiment of FIGS. 12 and 13 the registration members may be fixed to fixture 125.

As shown in FIGS. 12 and 13, a camera 130 may be located above slide 16. Camera 130 may acquire one or more images of slide 16 in which samples 18 can be seen. The locations of samples 18 in a coordinate system of controller 20 can then be determined from the locations at which the samples 18 appear in the images acquired by camera 130 using any suitable image-processing techniques. Various algorithms suitable for locating objects in images are well known and are therefore not described herein. Such algorithms may be applied by providing computer software executing on a data processor, by providing hardware that implements the algorithms or by some combination of these. To facilitate locating samples 18 it is desirable to illuminate slide 16 obliquely. For example, light may be directed onto slide 16 from a homogenous light source 132 at an angle of, for example, 45 degrees. This light is internally reflected in slide 16 and liquid coverslip 19. Samples 18 scatter light. This causes samples 18 to show up as bright spots against a dark background. Marks may be provided on the apparatus within a field of view of the camera for use in calibrating the camera.

The apparatus described above provides probe tips 12 that can hold small droplets of reagent. The reagent has a smaller overall affinity for the probe tip than it does for the sample. When the droplet of reagent is put in contact with a sample, the droplet adheres to the sample. When the droplet is adherent to the sample, he droplet will be pulled off of the probe tip if the probe tip is retracted. By approaching the sample in a manner that steps toward the sample and then steps back a sensor associated with the probe tip can detect when the droplet has adhered to the sample because the sensor can detect that the droplet has been pulled off of the probe tip when the probe is withdrawn. In some cases, the droplet may have such a strong affinity for the sample that it is drawn into or onto the sample. If this occurs strongly enough then it may not be necessary to approach the sample in a way that involves stepping back as the droplet will be pulled off from the probe tip as soon as it contacts the sample.

FIGS. 14 and 15 show an alternative mode of operation. These Figures show a probe tip 212 that has a pair of electrodes 244. Electrodes 244 are spaced far enough apart from one another that each electrode 244 retains a separate droplet 214 of a reagent as probe tip 212 is removed from a reservoir of the reagent. The volume of each small droplet of reagent is defined primarily by the diameter of each electrode 244.

A controller 220 monitors an electrical conductivity between electrodes 244. The electrical conductivity is initially very low, as indicated by line 221 because droplets 214 are not touching and electrodes 244 are electrically insulated from one another.

Probe tip 212 is then slowly lowered toward a sample 18 while monitoring the electrical conductivity between electrodes 244. As the droplets 214 of reagent on the electrodes contact sample 18, sample 18 is wetted and an electrical circuit is established between electrodes 244. This causes controller 220 to measure an increase in conductivity, as indicated by line 222 in FIG. 9. The increase of conductivity indicates that the reagent has been transferred to the sample 18. Upon detecting such an increase in conductivity, controller 220 can stop the advance of probe tip 212 toward the sample 18.

The methods and apparatus described herein may be applied, without limitation, to deliver reagents for immunohistochemical staining (IHC) or probes for fluorescence in situ hybridization (FISH). The samples may be, for example, individual tissue biopsies, fine needle aspiration biopsies that are arrayed as tissue cores, or groups of cells.

In some embodiments, an array of samples is provided by embedding an array of tissue biopsies in a block of paraffin. A thin slice of the paraffin block is placed onto a slide. The paraffin can them be removed, for example by applying standard techniques using ethanol and xylene, to leave the array of biopsies on the slide. A liquid coverslip such as a suitable oil coating can then be applied over the array of biopsies to prevent the biopsies from drying out.

It can be appreciated that devices as described above may be made and operated to provide a number of advantages. These include:

- An automated system may be controlled to apply different reagents to adjacent samples in an array of samples.
- Fluid crosstalk between array elements is prevented.
- Very tiny droplets of reagents may be dispensed, thereby reducing consumption of expensive reagents in comparison to batch methods.
- Droplets can be dispensed onto a sample that is covered by a liquid coverslip layer or a layer of an oily liquid.
- The probe tip does not need to contact the samples (unlike pin printers, for example). This is especially advantageous where the samples are fragile samples that might be damaged by contact.
- An automated system can deliver reagents to samples that are closely spaced apart on a high-density microarray slide.
- An IHC system that applies methods and apparatus as described herein can allow for customized tissue core pre-treatment incubation with reagents followed by application of antibody probes to specifically designated tissue cores or cell groups on a tissue or cell microarray. For example, these methods and apparatus can facilitate a protocol for immunohistochemical staining which includes customized application of small volumes of pre-treatment reagents to break protein cross linking, followed by small volume application of antibody probes to each specific tissue biopsy within the microarray.

Except as specifically recited in the appended claims, it is not mandatory that all or any of these advantages be provided by any specific embodiment of the invention.

In some cases it may be desirable to provide mechanisms for preventing fluid crosstalk between samples 18 in addition to or instead of a liquid coverslip. In such cases crosstalk can be prevented by placing the array of samples 18 on a hydrophobic substrate. The process used to bind samples to slides should be compatible with the hydrophobic substrate. For example, where the hydrophobic substrate comprises a coating on the surface of a slide and a paraffin process will be used to bind samples to the slide, the coating should be robust enough to withstand heating and immersion in a solvent during removal of paraffin from the samples.

In the alternative, hydrophobic boundaries between samples 18 may be applied after an array of samples has been loaded onto a reagent delivery system as shown for example in FIG. 12 and sample locations have been determined. Hydrophobic boundaries may be created, for example, by spotting a hydrophobic material onto the surface of a slide 16 with an inkjet-type spotter capable of dispensing hydrophobic fluid, or by using a contact/stamp method.

In cases where samples are sensitive to heat or humidity, sample preservation can be enhanced by strictly controlling both the temperature and humidity of the samples. Sample temperature can be controlled by thermally contacting the array backing to a cooler, for example, a Peltier cooler, and a temperature sensor, for example, a thermocouple. In some embodiments, the controller may be configured to operate the cooler to maintain a slide carrying a plurality of samples below a threshold temperature until the apparatus has applied reagent to a plurality of samples on the slide; and, subsequently warm the slide. A closed loop humidity control can also be provided if the microarray is enclosed so that a controlled atmosphere can be provided at the locations of the samples.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true scope.

Where a component (e.g. a controller, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

As will be apparent to those skilled in the art in the light of the foregoing disclosure, many alterations and modifications are possible in the practice of this invention without departing from the spirit or scope thereof. For example:

- A delivery device as described herein can be used to both pick up, and deposit fluidic reagents to each sample.
- It is not necessary that the samples be held fixed while the probe tip moves. All that is required is an ability to position a probe tip 12 relative to a sample 18. Samples 18 may be moved while probe tip 12 is held fixed or samples 18 may be movable in one or more dimensions while probe tip 12 is movable in one or more dimensions. For example, samples 18 and supplies of any required reagents may be supported on a two-axis adjustable stage. Probe tip 12 may be mounted on a one-axis stage. After the two-axis stage has been adjusted to align a sample with probe tip 12, the one-axis stage can be used to advance probe tip 12 toward the sample.
- By using smaller probe tips one can deposit smaller amounts of reagent. For example, by using probe tips having diameters on the order of 1 μm in diameter one can obtain droplets of reagent having volumes on the order of 1 femtoliter. Such small volumes of reagent could be used, for example, to treat single cells. Probes of such small sizes may be made by micromachining techniques.
- Dispensing apparatus as described herein may be used to deposit droplets of oily liquids. In this case, the probe tip should have an affinity for the oily liquid to be dispensed that is lower than an affinity of the oily liquid for the sample such that the droplet of oily liquid will adhere to the sample such that it will be pulled off of the probe tip if the probe tip is withdrawn and/or be pulled off of the probe tip by being absorbed into or onto the sample when the droplet touches the sample. In some cases it can be advantageous to provide on the probe tip oleophilic areas separated by an oleophobic area (e.g. by replacing the relatively hydrophilic areas with relatively oleophilic areas and by replacing the relatively hydrophobic areas with relatively oleophobic areas in the embodiments described above).

A probe tip does not necessarily have to have areas that are relatively hydrophilic and hydrophobic or relatively oleophilic and oleophobic. The surface of the end portion of a probe tip could be uniformly hydrophilic, hydrophobic, oleophilic and/or oleophobic as long as one or more droplets of the desired reagent can be carried on the probe tip.

Accordingly, the scope of the invention is to be construed in accordance with the substance defined by the following claims.

What is claimed is:

1. Apparatus for dispensing a reagent onto a sample, the apparatus comprising:
   a controller;
   a probe tip;
   a sensor comprising two or more exposed electrodes on the probe tip and a mechanism for monitoring electrical conductivity between the electrodes for detecting adhesion of a droplet of reagent on the probe tip, the sensor communicating with the controller;
   an actuator coupled to the probe tip and operative to advance the probe tip toward a sample and retract the probe tip from the sample under control of the controller;
   wherein the controller includes a logic mechanism that causes the controller to:
      advance the probe tip toward the sample until the sensor detects an alteration in an adhesion of the droplet to the probe tip; and,
      cease advancing the probe tip toward the sample in response to the detection of an alteration in an adhesion of the droplet to the probe tip.

2. Apparatus according to claim 1 wherein surfaces of the electrodes are hydrophilic.

3. Apparatus according to claim 1 wherein a surface of an area between the electrodes is hydrophobic.

4. Apparatus according to claim 1 wherein surfaces of the electrodes are oleophilic.

5. Apparatus according to claim 4 comprising an oleophobic area between the electrodes.

6. Apparatus according to claim 1 wherein one of the electrodes is annular and the other one of the electrodes is surrounded by the annular electrode.

7. Apparatus according to claim 1 wherein an end surface of the probe tip is flat.

8. Apparatus according to claim 1 wherein an end surface of the probe tip is concave.

9. Apparatus according to claim 1 wherein an end surface of the probe tip forms a dihedral.

10. Apparatus according to claim 1 wherein an end surface of the probe tip forms an acute angle with a side face of the probe tip.

11. Apparatus according to claim 1 wherein the probe tip comprises two members spaced apart from one another by an air gap.

12. Apparatus according to claim 11 wherein end surfaces of the two members are hydrophilic.

13. Apparatus according to claim 1 wherein the electrodes are spaced apart by an air gap.

14. Apparatus according to claim 13 wherein an end surface of at least one of the electrodes forms an acute angle with a side face of the electrode.

15. Apparatus according to claim 13 wherein a distance by which the electrodes are spaced apart is adjustable.

16. Apparatus according to claim 13 wherein an angle of one of the electrodes relative to the other one of the electrodes is adjustable.

17. Apparatus according to claim 1 wherein an end surface of the probe tip is generally round and has a diameter in the range of 0.01 mm to 5 mm.

18. Apparatus according to claim 1 wherein an end surface of the probe tip has a diameter of less than 1 mm.

19. Apparatus for dispensing a reagent onto a sample, the apparatus comprising:
   a controller;
   a probe tip;
   a sensor for detecting adhesion of a droplet of reagent on the probe tip, the sensor communicating with the controller;
   an actuator coupled to the probe tip and operative to advance the probe tip toward a sample and retract the probe tip from the sample under control of the controller;
   wherein the controller includes a logic mechanism that causes the controller to:
      advance the probe tip toward the sample until the sensor detects an alteration in an adhesion of the droplet to the probe tip; and,
      cease advancing the probe tip toward the sample in response to the detection of an alteration in an adhesion of the droplet to the probe tip;
   wherein the logic mechanism is configured to advance the probe tip toward the sample in a series of cycles, each cycle comprising advancing the probe tip toward the sample to an approach point and moving the probe tip away from the sample
   wherein the approach point is closer to the sample in successive cycles.

20. Apparatus according to claim 19 wherein the logic mechanism is configured to check an output of the sensor to determine whether there has been an alteration in an adhesion of the droplet to the probe tip after moving the probe tip away from the sample.

21. Apparatus according to claim 19 wherein the droplet projects from the probe tip by a droplet thickness and the logic mechanism is configured to cause the distance from the approach point to the sample to decrease between successive cycles by an amount that is less than the droplet thickness.

22. Apparatus according to claim 21 wherein the logic mechanism is configured to cause the distance from the approach point to the sample to decrease between successive cycles by an amount that is less than ¼ of the droplet thickness.

23. Apparatus according to claim 19 comprising a support for supporting a slide containing a plurality of samples wherein the sample is on the slide.

24. Apparatus according to claim 23 comprising a cooler located in thermal contact with the slide wherein the controller is configured to:
   operate the cooler to maintain the slide below a threshold temperature until the apparatus has applied reagent to a plurality of samples on the slide; and,
   subsequently warm the slide.

25. Apparatus according to claim 19 wherein the controller is configured to place an array of samples onto a substrate and to subsequently apply reagent to a plurality of the samples.

26. Apparatus according to claim 25 comprising a camera located to obtain digital images of a substrate carrying a plurality of samples, wherein the controller comprises an image processing mechanism that determines locations of the samples in the digital images and the controller uses the location of a selected sample determined by the image processing mechanism to align the probe tip with the selected sample.

27. A method for depositing a reagent onto a sample, the method comprising:
  forming a droplet of the reagent on a probe tip;
  placing the probe tip near the sample;
  advancing the probe tip toward the sample and monitoring for an alteration in adhesion of the droplet to the probe tip by monitoring an electrical conductivity between two or more electrodes on the probe tip;
  allowing the droplet to contact the sample and thereby altering an adhesion of the droplet to the probe tip;
  upon detecting the alteration in adhesion of the droplet to the probe tip, withdrawing the probe tip from the sample.

28. A method according to claim 27 wherein advancing the probe tip toward the sample comprises performing a series of cycles, each cycle comprising advancing the probe tip toward the sample to an approach point and then moving the probe tip away from the sample wherein a distance from the approach point to the sample decreases in successive cycles.

29. A method according to claim 27 wherein the droplet has a volume of less than 1 µl.

30. A method according to claim 29 wherein the droplet has a volume in the range of 1 nl to 1 µl.

31. A method according to claim 27 wherein forming a droplet of the reagent on the probe tip comprises dipping the probe tip into a volume of the reagent and withdrawing the probe tip from the volume of reagent.

32. A method according to claim 27 comprising providing a slide supporting a plurality of samples and repeating the method to apply a reagent to each of the plurality of samples.

33. A method according to claim 32 comprising applying a droplet of a different reagent to each one of the plurality of samples.

34. A method according to claim 32 comprising locating the samples by obtaining a digital image of the plurality of samples, and processing the digital image to determine locations of the samples.

35. A method according to claim 27 wherein advancing the probe tip toward the sample comprises advancing the probe tip through a liquid material.

36. A method according to claim 35 wherein the liquid material comprises an oily liquid.

37. A method for depositing a reagent onto a sample, the method comprising:
  forming at least one droplet of the reagent on a probe tip comprising first and second electrodes;
  placing the probe tip near the sample;
  advancing the probe tip toward the sample and monitoring electrical conductivity between the first and second electrodes;
  upon detecting an alteration in the electrical conductivity between the first and second electrodes, halting advance of the probe tip toward the sample.

38. A method according to claim 37 wherein detecting an alteration in the electrical conductivity between the first and second electrodes comprises detecting an increase in conductivity.

39. A method according to claim 38 comprising applying a separate droplet of the reagent on each of the first and second electrodes prior to advancing the probe tip toward the sample.

40. A method according to claim 37 wherein detecting an alteration in the electrical conductivity between the first and second electrodes comprises detecting a decrease in conductivity.

41. A method according to claim 37 wherein the reagent comprises an aqueous reagent.

42. A method according to claim 41 wherein advancing the probe tip toward the sample comprises advancing the probe tip through a liquid material.

43. A method according to claim 42 wherein the liquid material comprises an oily liquid.

44. A method according to claim 37 wherein advancing the probe tip toward the sample comprises performing a series of cycles, each cycle comprising advancing the probe tip toward the sample to an approach point and then moving the probe tip away from the sample wherein a distance from the approach point to the sample decreases in successive cycles.

45. A method according to claim 44 wherein the droplet has a volume of less than 1 µl.

46. A method according to claim 45 wherein the droplet has a volume in the range of 1 nl to 1 µl.

47. A method according to claim 44 wherein forming a droplet of the reagent on the probe tip comprises dipping the probe tip into a volume of the reagent and withdrawing the probe tip from the volume of reagent.

48. A method according to claim 47 comprising providing a slide supporting a plurality of samples and repeating the method to apply a reagent to each of the plurality of samples.

49. A method according to claim 48 comprising applying a droplet of a different reagent to each one of the plurality of samples.

50. A method according to claim 48 comprising locating the samples by obtaining a digital image of the plurality of samples, and processing the digital image to determine locations of the samples.

* * * * *